US00PP17772P2

(12) United States Plant Patent
Anatriello

(10) Patent No.: US PP17,772 P2
(45) Date of Patent: May 29, 2007

(54) ***ABUTILON* PLANT NAMED 'ATN YB5'**

(50) Latin Name: *Abutilon vexillarium*
Varietal Denomination: ATN YB5

(75) Inventor: Lucilene Anatriello, Sao Jose do Rio Preto (BR)

(73) Assignee: Athena Mudas, LTDA, A Brazilian Corporation, Sao Jose Do Rio Preto (BR)

( * ) Notice: Subject to any disclaimer, the term of this patent is extended or adjusted under 35 U.S.C. 154(b) by 0 days.

(21) Appl. No.: 11/266,037

(22) Filed: Nov. 4, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
(74) *Attorney, Agent, or Firm*—Albert O. Cota

(57) ABSTRACT

A new and distinct *Abutilon* plant cultivar is disclosed, characterized by bright yellow flowers, large, glossy leaves, an upright, vigorous growth habit and a tall plant height. The new variety is an *Abutilon,* and naturally blooms from April to September.

1 Drawing Sheet

Latin name of the genus and species: *Abutilon vexillarium.*
Variety denomination: 'ATN YB5'.

BACKGROUND OF THE INVENTION

The new cultivar is a product of a planned breeding program. The new variety was discovered as a naturally occurring whole plant mutation. The instant plant was found as a single plant from a planting of more than 1000 plants of '*Abutilon* Yellow' by Lucilene Anatriello in February 2004 in Sao Jose do Rio Preto, Brazil.

Asexual reproduction of the new cultivar 'ATN YB5' by vegetative cuttings was performed in Sao Jose do Rio Preto, Brazil and has shown that the unique features of this cultivar are stable and reproduced true to type it successive generations.

SUMMARY OF THE INVENTION

The cultivar 'ATN YB5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ATN YB5.' These characteristics in combination distinguish 'ATN YB5' as a new and distinct *Abutilon* cultivar:

1. Tall, vigorous growth habit;
2. Large green leaves;
5. Long blooming period; and
6. Bright yellow petals.

Plants of the new cultivar 'ATN YB5' are similar to plants of the parent, '*Abutilon* Yellow', in most horticultural characteristics, however, plants of the new cultivar 'ATN YB5' are taller and more vigorous than the parent. Additionally, the new variety has larger leaves as well as more leaves per lateral branch. The new variety resists dropping leaves and blooms one month longer than the parent variety. The new variety 'ATN YB5' also has brighter yellow petals.

There is no similar commercial varieties available to compare to 'ATN YB5'.

BRIEF DESCRIPTION OF THE PHOTOGRAPH

The accompanying photograph in FIG. 1 illustrates in full color a typical plant of 'ATN YB5' grown in an outdoor garden with a grouping of 15 other plants. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'ATN YB5' plants grown outdoors in Oxnard, Calif. from November 2004 to August 2005. The growing temperature ranged from 10° C. to 15° C. at night to 12° C. to 30° C. during the day. Measurements and numerical values represent averages of typical flowering types.

Botanical classification: *Abutilon vexillarium* cultivar 'ATN YB5.'

PROPAGATION

Time to rooting: 15 to 21 days at approximately 21° C.
Root description: Fine, fibrous.

PLANT

Growth habit: Upright shrub.
Height: Approximately 170.18 cm.
Blooming period: April to September.
Plant spread: Approximately 73.66 cm.
Growth rate: Highly vigorous.
Branching characteristics: Moderate upright branching.
Length of lateral branches: Approximately 150 cm.
Diameter of lateral branch: Approximately 0.8 cm.

Color of lateral branch: Near Green 137A.
Number of leaves per lateral branch: Approximately 46.
Age of plant described: Approximately 221 days.

FOLIAGE

Leaf:
*Arrangement.*—Alternate.
*Average length.*—Approximately 9.2 cm.
*Average width.*—Approximately 13.5 cm.
*Shape of blade.*—Palmate.
*Apex.*—Acuminate.
*Base.*—Hastate.
*Attachment.*—Stalked.
*Margin.*—Entire.
*Texture of top surface.*—Lightly pubescent.
*Texture of bottom surface.*—Smooth.
*Internode length.*—Approximately 5 cm.
*Color.*—Young foliage upper side: Near R.H.S. Green 137A. Young foliage under side: Near Green 137C. Mature foliage upper side: Near Green 137A. Mature foliage under side: Near Green 137C.
*Venation.*—Type: Palmately net. Venation color upper side: Near Yellow-Green 144C. Venation color under side: Near Yellow-Green 144C.
Petiole:
*Average length.*—Approximately 6.6 cm.
*Color.*—Near Yellow-Green 144B.
*Diameter.*—Approximately 0.01 cm.

FLOWER

Bud:
*Bud shape.*—Spherical.
*Bud length.*—Approximately 2 cm.
*Bud diameter.*—Approximately 1.2 cm.
*Bud color.*—Near Near Yellow 12A.
Flower:
*Shape.*—Bell-shape, with five unfused petals.
*Facing direction.*—Down.
*Type.*—Simple.
*Aspect.*—Concave.
*Diameter of entire flower.*—Approximately 3.5 cm.
*Length of flower.*—Approximately 3.9 cm.
Petals:
*Shape of petal.*—Ovate.
*Length of petal.*—Approximately 3.5 cm.
*Width of petal.*—Approximately 3 cm.
*Apex shape of petal.*—Obtuse.
*Petal margin.*—Entire.
Color:
*Upper surface at first opening.*—Near Yellow 12B.
*Upper surface at maturity.*—Near Yellow 12A.
*Upper surface at fading.*—Near Yellow 13C.
*Under surface at first opening.*—Near Yellow 11A.
*Under surface at maturity.*—New Yellow 12A.
*Under surface at fading.*—New Yellow 13C.
Fragrance: None.

SEPAL

Number: 5; fused at base.
*Sepal shape.*—Lanceolate.
*Sepal length.*—Approximately 2.2 cm.
*Sepal width.*—Approximately 0.06 cm.
*Apex shape.*—Acute.
*Margin.*—Entire.
*Color.*—Inside sepal color near R.H.S. Yellow-Green 145B and outside sepal color near R.H.S. Yellow-Green 145A.
*Reproductive organs.*—1 normal pistil and over 100 normal stamens.
Peduncle:
*Width.*—Approximately 0.01 cm.
*Length.*—Approximately 14.6 cm in length.
*Angle to stem.*—Downward from stem at 135 degree angle.
*Strength.*—Strong.
*Texture.*—Smooth.
*Color.*—Near Yellow-Green 143B.

REPRODUCTIVE ORGANS

Number of pistils per floret: 1.
Stigma shape: Globular.
Stigma color: Near Yellow-Orange 14B.
Style color: Near Yellow 8A.
Style length: Approximately 3.4 cm.
Stamens: Over 100 stamens.
Anther shape: Globular.
Anther color: Near Yellow 14A.
Pollen color: Near Yellow 14A.

OTHER CHARACTERISTICS

Disease resistance: Neither resistance nor susceptibility to diseases or pests has been observed in this variety.
Drought tolerance and cold tolerance: Hardy to 23° F. (−5° C.) and will generally grow back from the base if the top is frozen. No drought tolerance has been observed.
Fruit/seed production: Seed production has not been observed.

What is claimed is:

1. A new and distinct *Abutilon* plant cultivar named 'ATN YB5' characterized by yellow flowers, large glossy leaves, an upright, vigorous growth habit and a tall plant height.

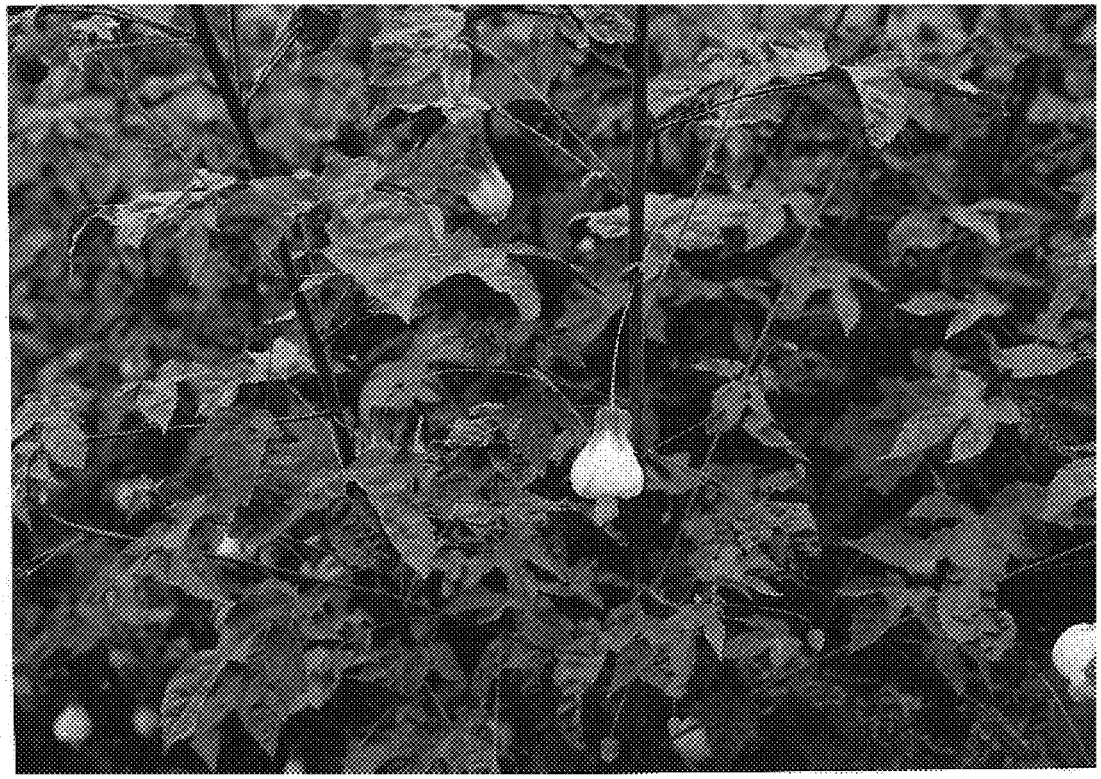

* * * * *